United States Patent [19]

Dougan

[11] Patent Number: 5,248,771

[45] Date of Patent: Sep. 28, 1993

[54] PROCESS FOR PREPARING NO-CARRIER-ADDED RADIOHALOGENATED VINYL NUCLEOSIDES

[75] Inventor: Hayes Dougan, Vancouver, Canada

[73] Assignee: Triumf, Vancouver, Canada

[21] Appl. No.: 721,383

[22] Filed: Jun. 26, 1991

[51] Int. Cl.$^5$ .................... C07H 19/09; A61K 43/00; A61K 31/70
[52] U.S. Cl. ................. 536/28.54; 536/55.3
[58] Field of Search ..................... 536/23, 55.3, 28.54; 514/49, 50; 252/625; 534/10; 436/804

[56] References Cited

U.S. PATENT DOCUMENTS 4,211,773  7/1980  Lopez et al. ..................... 514/49
4,386,076  5/1983  Machida et al. ................... 514/50

OTHER PUBLICATIONS

Samuel et al., Int. J. Appl. Radiat. Isot. 35(11): 1049–1052, 1984.
Verbruggen et al. Appl. Radiat. Isot. 37(4): 355–357, 1986.
Robbins et al. J. Med Chem. 34:2275–2280, 1991.

Primary Examiner—Johnnie R. Brown
Assistant Examiner—Gary L. Kunz
Attorney, Agent, or Firm—Griffin, Butler, Whisenhunt & Kurtossy

[57] ABSTRACT

Reacting [*X]X- with YVaraU in the presence of a cuprous ion catalyst under anaerobic and reducing conditions produces [*X]XVaraU, where *X is a radioactive halogen, Y is a second halogen, X and Y are different halogens, and XVaraU is 1-($\beta$-D-arabinofuranosyl)-5(E)-(2-halogenovinyl) uracil, the halogen of which is X. The reaction produces an effective administrable form of [*X]XVaraU for use in diagnosis and treatment of herpes virus infections.

15 Claims, No Drawings

PROCESS FOR PREPARING NO-CARRIER-ADDED RADIOHALOGENATED VINYL NUCLEOSIDES

The present invention relates to antiviral radiohalogenated vinyl nucleoside compositions which may be used for both diagnostic and therapeutic purposes, as well as methods of production and methods of use thereof. The compositions have high radiochemical concentrations of antiviral agent, are essentially free of interfering by-products and have high specific radioactivity. More particularly, the invention so relates to radiohalogenated vinyl arabinosyl uracil.

BACKGROUND OF THE INVENTION

The structural formula of halogenated vinyl arabinosyl uracil is shown below:

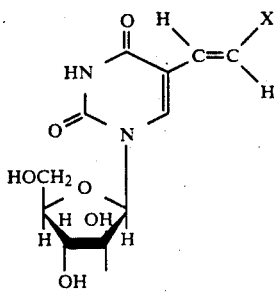

where X is halogen.

The compounds are properly named 1-($\beta$-D-arabinofuranosyl)-5(E)-(2-halogenovinyl) uracil, but are commonly referred to as "XVaraU", where X is halogen. When the compounds are radiohalogenated, the common designation is [*X]XVaraU, where *X represents the particular radiohalogen.

In regard to the halogen, while any of the halogens can be substituted on the vinyl group, the preferred radiohalogens are iodine and bromine. Certain radioisotopes of the halogens have half lives and modes of decay which limit patient dosage. Further, the gamma ray energy of some isotopes is better suited to detection devices. Therefore, some halogens and isotopes are either more useful or more practical or more available or less expensive than others. Thus, the invention will be described mainly in connection with the better suited and preferred halogens, i.e. iodine and bromine, and in regard to preferred isotopes thereof.

The invention is useful in diagnosis of and treatment of viral diseases, especially viral diseases which adversely affect the brain, and more specially, such diseases where the presence of the virus is difficult to detect by external examination of the human body. A notable example of the foregoing is viral encephalitis in man. Diagnosis of viral encephalitis is difficult because accurate methods for the non-invasive detection of the virus in the host brain cells have not been developed, and, as can be easily appreciated, the clinician is most reluctant to harvest brain tissue from a patient unless encephalitis is most strongly suspected.

An example of the foregoing, and one of the infections specifically exemplified herein, is HSV type 1 herpes virus, which is a major cause of severe sporadic encephalitis in man. Early symptoms of HSV encephalitis, include personality change, behavioral disturbance, seizures and mutism, and are anatomically explained by the predilection for the infectious process to involve the medial temporal lobe, orbital frontal lobe and other "limbic" areas of the brain. Late in the disease, destruction of these and other areas of the brain readily indicates the presence of the disease, but early in the disease, when diagnosis and institution of therapy are most important, such symptoms may be due to other causes, such as reversible physiological disturbance. It is to this early phase of such infections that the present invention is directed, since it is during this early phase, especially the first 72 hours after the onset of symptoms, that effective antiviral chemotherapy may be instituted.

A major impediment to effective early management of such infections, e.g. HSV encephalitis, is the lack of a reliable, non-invasive test which will allow early diagnosis. Unfortunately, present neurodiagnostic studies such as CT and radionuclide scanning may yield normal results early in such diseases and viral serology is only retrospectively useful, and even then may not be definitive. At present, a brain biopsy is the only definitive means of early diagnosis, but the biopsy is a major medical procedure. Therefore, the clinician is left with a difficult decision which may result in delayed or inappropriate therapy. Clearly, there is a need for an improved non-invasive diagnostic method for diseases of this nature.

An early attempt at providing such diagnostic methods is disclosed in U.S. Pat. No. 4,211,773 to Price. Price proposed a non-invasive diagnosis for HSV-1 encephalitis as follows. Selective uptake by infected cells of a radioactive (gamma ray emitting) antiviral drug serves as a substrate for virus-coded thymidine kinase. The "trapped" phosphorylated radioactive antiviral compounds can then be visualized using gamma ray scintigraphy or PET imaging. Price made the specific proposal that radiolabelled 5-substituted 1-(-2'deoxy-2'substituted)arabinofuranosyl pyrimidine nucleosides could be useful as tracers for such a scintigraphic diagnosis. Prompted by the disclosure of Price, others prepared and assayed potential radionucleoside tracer compounds of the anti-herpes class. Unfortunately, it was found that none of the radiotracer compounds was suitable, for a variety of complex reasons.

The present invention is concerned with derivatives of XVaraU and especially I- and BrVaraU. Recently, IVaraU was shown (along with BrVaraU) as an unlabelled antiherpes drug.

U.S. Pat. No. 4,386,076 discloses XVaraU and shows experimental results in halogenating the vinyl arabinosyl uracil with bromine and chlorine to produce the corresponding BrVaraU or ClVaraU. The patent, however, provides no experimental details in regard to IVaraU.

However, recently S. Sacks (see Abstract 97 of the 1988 proceedings of the Interscience Conference on Antimicrobial Agents and Chemotherapy) disclosed that [$^{123}$I]IVaraU is concentrated in herpes infected tissue. This compound is an arabinosyl uridine derivative, not a 2'substituted 2'deoxy arabinosyl uridine, as specified in the Price patent. Thus, the compound [$^{123}$I]IVaraU promised to become important as a practical radiotracer for herpes.

While [$^{123}$I]IVaraU is, therefore, a valuable compound for the above purposes, it was discovered that this compound and related [*X]XVaraU compounds also have serious disadvantages when prepared in administrable composition form. In this regard, certain criteria must be satisfied in order to provide a satisfactory administrable form. Considering the high cost of $^{123}$I and the rather short half life of 13.3 hours, it is firstly necessary that radiolabelling utilizing $^{123}$I be nearly quantitative and secondly that the process of labelling must be of short time duration. Thirdly, the labelling process must be straightforward and with few complications, so as to be conductible by technicians, e.g. hospital technicians (nuclear medicine technologists). A striking property of IVaraU is that it is highly physiologically potent per unit weight; for example, it effectively inhibits herpes virus at very low concentrations (approximately $1 \times 10^{-9}$ g/mL, depending on the strain of herpes virus). Thus, fourthly, the administrable form must be in low molar concentrations but of high specific radioactivity. Fifthly, a "no carrier added" administrable form is, therefore, also required for best results. The latter would be extremely desirable for demonstration of anti-herpes therapy by the Auger method, as discussed below. Sixthly, considering [*I]IVaraU as a radiopharmaceutical, it is necessary that a pure administrable form be provided, i.e. free from accompanying by-products (for example, the isomer must be trans; the cis isomer is not valuable). These six criterion are, therefore, necessary for an acceptable administrable form.

Unfortunately, the literature on iodolabelling of other similar nucleosides indicates low radiochemical yields and significant decomposition. The literature on unlabelled arabinosyl uridines indicates that arabinosyl uridines are particularly unstable to heating; it is thought that the 2'hydroxy group of arabinose reacts readily with the pyrimidine base.

In view of the foregoing, efforts to produce a satisfactory administrable form of [*I]IVaraU have produced less than desirable results as judged by the above criteria, and it has become clear that a different approach from that of the prior art is required. In one such attempt, radiolabelling of IVaraU employed a trimethyl silyl vinyl precursor, dichloro iodobenzene [$^{123}$I]NaI, and an unlabelled NaI added carrier. While useful [$^{123}$IVaraU is produced, the radiochemical yield is far too low, i.e. approximately 10%, and the specific radioactivity is also low, since the NaI carrier was added. Further, the product is accompanied by many unidentified contaminants, i.e. by-products. Thus, the administrable form of the compound produced by that reaction is far less than desirable, according to the above criteria.

Accordingly, it would be of substantial advantage to the art to provide an administrable form of [*]XVaraU which meets or substantially meets the above criteria of an acceptable administrable form and to provide a process for production thereof, as well as methods of use thereof.

BRIEF DESCRIPTION OF THE INVENTION

The present invention is based on several primary and several subsidiary discoveries. First, it was discovered the radioactive halide [*]X— can be substantially quantitatively converted to [*]XVaraU in a short time with no reaction complication by use of certain copper catalyst, as described below. Second, it was discovered that the radiochemical products are essentially pure and essentially free of by-product contaminants. Third, it was discovered that the so-labelled products can be produced in low molar concentrations but with high specific radioactivity. Fourth, it was discovered that the reaction and, hence, the administrable form could be prepared without the use of a carrier (a "no carrier added" product). As a subsidiary discovery, it was found that the reaction could be carried out at elevated temperatures and that those temperatures did not decompose the [*]XVaraU product. Further, as a subsidiary discovery, it was found that the copper catalysis must be in the form of a cuprous ion. Finally, as a subsidiary discovery, it was found that the catalyzed reaction must be an exchange reaction between [*]X- and YVaraU under anaerobic and reducing conditions, where X and Y are different halogens.

Thus, broadly stated, in one aspect, the invention provides a process for producing [*]XVaraU, comprising reacting [*]X- with YVaraU in the presence of a cuprous ion catalyst under anaerobic and reducing conditions, where *X is a radioactive halogen, Y is a halogen, X and Y are different halogens, and XVaraU is 1-($\beta$-D-arabinofuranosyl)-5(E)-(2-halogenovinyl) uracil, the halogen of which is X. An example of the reaction is as follows:

$$[^*]NaX + YVaraU \rightarrow [^*X]XVaraU + NaY$$

where X and Y are different halogens, e.g. where sodium iodide is reacted with a bromo VaraU.

There is also provided an antiviral and diagnostic composition useful for detecting and treating a virus infection in an animal, which virus utilizes animal brain cells as the primary host cells, comprising an administrable form of [*]XVaraU wherein the composition contains no added carrier, no substantial amount of reaction by-products and wherein *X is a radioactive halogen and XVaraU is 1-($\beta$-D-arabinofuranosyl)- 5(E)-(2-halogenovinyl) uracil, the halogen of which is X.

Further, the invention provides a method of diagnosis of an animal for viral infection, comprising administering to the animal a scintillating effective amount of the above-noted composition and preparing a scintigram of the animal.

Additionally, there is provided a method for treating an animal having the herpes virus infection comprising administering to the animal a virus-destructive effective amount of the above composition.

Finally, there is provided a method of diagnosis of an animal for virus infection comprising admixing a sample of the blood of the animal, tissue culture cells susceptible to the virus infection, and a scintillating effective amount of the above composition and counting the radioactive uptake in the tissue culture cells.

DETAILED DESCRIPTION OF THE INVENTION

As noted above, the process of the invention for producing [*]XVaraU comprises reacting [*]X-(halide) with YVaraU in the presence of a cuprous ion catalyst under anaerobic and reducing conditions, e.g. in the presence of a reducing agent. Anaerobic conditions, of course, means the essential absence of oxygen, and this can be achieved by a variety of methods, well known to the art, but more conveniently, the head space of the reaction vessel is simply provided with a blanket of inert gas. The head space may be flushed with the inert gas, and then sealed, or a continuous flush of the inert gas may be provided, or the head space of the reaction vessel may be evacuated and then flushed with an inert gas. The particular inert gas is not critical, but conventional argon or nitrogen are quite adequate in this regard. Also, reducing agents, such as ascorbic acid, SnSO$_4$ or $^{2,5}$dihydroxy benzoic acid, or mixtures thereof, are employed to remove the last traces of oxygen during the reaction.

As can be appreciated, it is important that the present reaction proceed to nearly quantitative results in a short time, and to achieve that effective reaction, the copper catalyst must be in the form of cuprous ions. If oxygen is present, of course, cuprous ions in the reaction medium will oxidize and the reaction efficiency will greatly decrease. When the reaction efficiency greatly decreases, not only will the yield be lower, but unwanted by-products of the reaction will occur, e.g. unreacted materials, side reaction products, isomers, etc. When such occurs, the composition which results will not consist essentially of the [*]XVaraU but will contain a substantial amount of reaction by-products which are not within the formula [*]XVaraU. As noted above, low yields and unwanted by-products are not within the criteria for an administrable form, and such would not be acceptable.

As noted above and for the same reason stated above, it is desirable to carry out the reaction in the presence of a reducing agent. While a wide variety of reducing agents may be used, ascorbic acid is well known for its ability to convert Cu$^{+2}$ ions to Cu$^{+1}$ ions and is, in addition, an excellent dry powder medium for trituration of microgram quantities of reagents in the absence of oxygen or water. Ascorbic acid is, therefore, a preferred reducing agent. On the other hand, radioiodine is better kept in the iodide state by use of Sn$^{++}$ salts and anaerobic conditions. Hence, it is desirable to have a tin compound in the reaction medium. Thus, SnSO$_4$ is valuable as the reducing agent and for maintaining the iodide state and is, therefore, a preferred reducing agent. Indeed, ascorbic acid and a tin compound, e.g. SnSO$_4$, therefore, may be used in combination as reducing agents. However, as noted above, other reducing agents, such as dihydroxy benzoic acid, function satisfactorily and may be used.

The reaction is also advantageously carried out in the presence of an anion since appropriate anions will solubilize high concentration of Cu$^{+1}$ ions. While a wide variety of pharmacological anions are known to the art, the precursor, e.g. a cuprous salt, should be somewhat soluble, e.g. somewhere about at least 150 $\mu$g/ml. For example, earlier workers suggested the use of the cuprous halides, but these are not sufficiently soluble and should be avoided. It is preferred that the anion be a sulfate, acetate or phosphate anion. It is more preferred, however, that the anion is a sulfate anion. Ascorbic acid also gives rise to anions; therefore, multiple anion species are likely to be present, solubilizing the cuprous ion.

The exchange reaction operates best under acidic conditions near the pH range 1.5 to 3.5. However, for example, commercial radioiodine arrives in an alkaline solution, e.g. 0.1N NaOH, as a rule. Therefore, a solution of dilute H$_2$SO$_4$, with other salts in the sulphate form, is a practical way to neutralize the alkaline radioiodine solution as well as provide the desired sulfate anion for solubilizing the cuprous salts, as noted above. An additional potential danger in using other acids for neutralization is that certain organic acids, such as acetic acid, will convert, for example, radioiodide into a volatile form which may be lost on nitrogen or argon flushing of the reaction. Dilute sulfuric acid does not cause significant volatilization of the radioiodine.

The foregoing is also convenient in regard to the formation of the catalyst. Thus, while a wide variety of methods are known in the art for producing cuprous ions, it is most convenient for the cuprous ion catalyst to be provided in situ in the reaction medium by a copper salt precursor. As can therefore be appreciated, for example, when the copper salt precursor is CuSO$_4$, that precursor fits well with the use of sulfuric acid, as discussed above.

Conveniently, the reaction is carried out in a solvent, and any pharmacological solvent may be used, so long as the solvent is suitable for the starting reaction mixture. However, the solvent is conveniently water, or other common solvents such as ethanol or tert. butyl alcohol, but since water functions well as the solvent, it is the preferred solvent for obvious reasons.

As noted above, the present process may be carried out at elevated temperatures, without decomposition or destruction of the reaction product. This is, of course, a very important point, in that the elevated temperatures allow the reaction to go to essentially quantitative results in a reasonably short time, and at the same time, the elevated temperatures may be sufficiently high as to sterilize the reaction medium. While the reaction will proceed at low temperatures, e.g. 20° C., for obtaining quantitative results in a short time, the temperature of the reaction should be at least 50° C., and more preferably at least 75° C., with a preferred elevated reaction temperature of about 100° C. or greater and up to about 125° C.

Conveniently, the temperature is carefully controlled by a conventional laboratory heating block, but a water bath or other means may be employed if desired.

It will be appreciated that the above-described reaction is, in the more general sense, a halogenation reaction, and more particularly, a halogen addition reaction, and even more precisely a halogen exchange reaction. The literature describes many conditions for halogenation that are effective with quantities of "gram" scale. The better method may depend upon chemical functionality and other considerations in a particular case.

A new set of problems was encountered with "carrier-added" level radioiodinations and radiohalogenations. These reactions often involve 1 microgram to 1 milligram of radiohalogen. High yielding effective reactions of this type were developed from the mid 1970's to date and are still elusive with some radiopharmaceuticals.

A still more challenging reaction is the "no-carrier-added" reaction in terms of high yield and specificity. Progress was made during the 1980's with "no-carrier-added" levels of reactions, which may involve a few nanograms of radiohalogen. "No-carrier-added" radioiodination reactions are still under development today.

In the specific case of IVaraU, it happens that the "gram" scale synthesis is so difficult that no explicit description of a synthesis has appeared in the literature. The present preparation is at the "no-carrier-added" level, so it is an advance in the area. U.S. Pat. No. 4,386,076 refers to IVaraU but does not describe a synthesis; the initial disclosure by S. Sacks, referenced above, referred to the "carrier-added" [$^{123}$I]IVaraU from the trimethylsilylvinyl precursor.

Thus, in a general sense, the present process involves cuprous ion catalysis in a reaction with a radiohalogen, especially, radioiodine, by nucleophilic exchange, most preferably using a bromo vinyl or iodovinyl precursor. Such an exchange has some literature basis, e.g. U.S.

Pat. No. 3,814,769 shows radioiodide exchange reactions with aryliodide compounds. Thus, the general process is applied to bromo or iodo aryl precursors, although there are examples relating to radioiodination of (unlabelled) iodo vinyl precursors (e.g. iodo stilbestrol and iodo vinyl deoxy uridine). As another example, Belgian Patent BE899739 applied the general process to radioiodination of bromo and iodo aryl unlabelled precursors. The reaction conditions allowed higher yields in shorter times under mild conditions, in contrast to the earlier work. Mertens, et al (Eur. J.N.M. (1987) 380-381) wrote that in copper (II) salt mediated radiolabelling, breakdown products and $^{123}I_2$ can result, giving undesirable reaction by-products.

The present process, as described above, provides required conditions with, most preferably, bromo vinyl ara U precursor to make [$^{125}$, $^{123}$I]IVaraU and similar compounds. Such a reaction has not been described in the literature, probably because of one special problem. It appears that BrVaraU and other halogen vinyl pyrimidine nucleosides are less robust and stable compound than the aryl halides cited in most of the prior literature on radiolabelling. Thus, in a more specific sense, for example, such compositions of [$^{125}$I, $^{123}$I]IVaraU have not been described in the literature, nor has a process for so labelling using cuprous ion catalysis. Accordingly, in this general sense, while the literature provides some mild hints that copper ion catalysis might be applicable to cause a reaction, it does not teach that the reaction with cuprous ions is better than other literature techniques or that the reaction will result in a composition having the above criteria, especially nearly quantitative yields and short reaction times. For example, the cited exchange labelling employing cuprous chloride and deoxy iodovinyl deoxyuridine required 20 hours and produced only 45% yield with $^{131}$I($T_{\frac{1}{2}}$ 8 days). The application to $^{123}$I($T_{\frac{1}{2}}$ 13 hours) would be calculated to produce even a lower yield, i.e. approximately 16%, due to significant decay loss. Use of a bromo vinyl precursor would be expected to produce a significantly lower yield again because the exchange of iodide is thermodynamically favored compared to the exchange of bromide. Moreover, in the $^{131}$I case, cited above, substantial reaction by-products were reported, so that the product was not usable. In addition, the product could not be considered a "no-carrier-added" product.

Thus, it was surprising and unexpected that the present process, using a cuprous ion catalyst, would produce such dramatic and unexpected results, and that the reaction could produce a composition which meets all of the above criteria.

The particular halogens of the halogen replacement reaction, as described above, also affect the results of the reaction. The substances IVaraU and BrVaraU attracted attention to Br and Iodine because IVaraU and BrVaraU were highly potent in vivo per unit weight, and because they appeared metabolically stable in vivo (by comparison ClVaraU and FVaraU are less potent in vivo, while astatine-VaraU has not been tried). It is well known that radioiodines have certain practical characteristics: several are commercially available, $^{123}$I and $^{131}$I have suitable gamma ray energies and half lives for scintigraphic imaging analysis with patients using commercial imaging equipment, while $^{125}$I has suitable gamma ray energies and half life for in vitro work. The radiobromines have similar practical advantages, but appear less desirable by these practical criteria than the radioiodines. (Cl, F, and At radioisotopes would also have practical disadvantages.) When it was decided that IVaraU was of interest, the initial radiolabelling of the trimethylsilylvinyl precursor was very low yielding and gave by-products—it was not a recommendation for $^{123}$I.

Thus, the present invention is focused towards particular radiohalogens for the halogen replacement reaction. Pharmacological considerations pointed to IVaraU and BrVaraU as desirable radiopharmaceuticals and, hence, the relevance of radioiodines and radiobromines. Moreover, these latter radiohalogens offered useful decay and availability characteristics. Thus, the problem addressed with the present invention is to bring about exchange conditions with essentially quantitative yields, no reaction complications, and in a short time required for completion.

In this latter regard, a short time is defined as the reaction going to completion in less than 5 hours and preferably less than 3 hours. Further in this regard, an essentially quantitative yield is defined as at least about an 85% yield and preferably at least a 90% yield. Thus, iodine and bromine as the halogens of the reaction ar most important to reaching such quantitative yields with short reaction time and straightforward reactions. Further, in this regard, the reaction is far better conducted where *X is iodine and Y is bromine. Further, for the most useful radiolabelled products in the resulting composition, it is preferred that *X is $^{123}$I, $^{125}$I or $^{131}$I, and most preferably $^{123}$I and $^{125}$I. These three radioactive iodine substituents provide very good results, with nearly perfect results provided by $^{123}$I and $^{125}$I.

Turning now to the compositions themselves, in one aspect of the invention, the composition is a diagnostic composition for detecting virus infection in an animal, which virus utilizes animal brain cells as the primary host. As explained above, it is in connection with such diagnosis that the present invention has particular applicability, in view of the dilemma imposed on the clinician in early detection of such viral infections of the brain, i.e. the danger of a brain biopsy versus no detection. In view of the above-described criteria, and for the reasons explained above, this composition contains no added carrier. The nearly quantitative yields or essentially quantitative yields produced by the present reaction provide the composition in a most desirable form, and for that reason that form should not have any carrier added thereto. The addition of a carrier will decrease the otherwise desirable properties of the composition, as described above in connection with the criteria. In the usual sense, "carrier" refers to material such as water. However, a specialized radiochemical meaning is intended herein. In the case where there is a certain pure radioactive compound which contains a radioisotope of interest, e.g. $^{123}$I, then "carrier" refers to those molecules which accompany the radiochemical compound and which are identical in every aspect of molecular structure to the radioactive molecule, except for the fact that the stable isotope, e.g. $^{127}$I, is present instead of the analogous radioisotope.

"Carrier" can be added deliberately by two methods. One method is to add the unlabelled compound of interest directly, e.g. to prepare [$^{123}$I]IVaraU by exchange using unlabelled IVaraU as a substrate; the great excess of unlabelled IVaraU could never be removed. Carriers of the first type may be acceptable when the specific radioactivity of the product is not important. The second method is to add the stable isotope in a simple chemical form which can react to give the stable molecule of interest, while the synthesis of the radioactive molecule is occurring at the same time, e.g. to add [$^{127}$I]NaI during the synthesis of [$^{123}$I]IVaraU from BrVaraU or else from the trimethylsilylvinyl precursor. Carriers of the second type are frequently added to increase the radiochemical yield of a given reaction; it was necessary with the trimethylsilylvinyl precursor.

"No-carrier-added", simply, means that no attempt was made to add carrier deliberately, as in the previous paragraph.

The purpose of "no-carrier-added" compositions is to have high specific radioactivity of the product. With halogens such as iodine, there is little free halogen in the environment; a high specific radioactivity product can be obtained by a no-carrier-added strategy and use of clean reagents.

There are several advantages to the use of high specific radioactivity radiopharmaceuticals. When the number of receptors or relevant metabolizing enzymes is limited, it is necessary that the number of radioactive molecules be small, i.e. that the specific radioactivity be high, in order that a scintillating quantity of the radiopharmaceutical will be confined in the target organ to give a useful scintigraphic image; otherwise, most of the activity will be uniformly distributed in the blood. Another advantage is when the radiopharmaceutical has a potent physiological effect (this is the case with IVaraU), the physiological effect can be minimized by having the highest available specific radioactivity.

A practical definition of no-carrier-added/high specific activity is a radiopharmaceutical composition which satisfies several conditions: (1) no carrier was deliberately added to the final composition, (2) no carrier (direct or indirect) was deliberately added during the radiolabelling of the radiopharmaceutical, and (3) a good commercial quality no-carrier-added radiohalide solution was used for the radiolabelling reaction.

For essentially the same reasons, the composition will have no substantial amount of reaction by-products, since those by-products not only indicate an uneconomical and incomplete reaction, but those by-products, particularly decomposition by-products, can interfere with the usefulness of the composition in diagnosis or treatment of such viral diseases.

The term "no substantial amount of reaction by-products" refers to molecules whose structure is similar to that of XVaraU, but not identical. These could include breakdown products, especially free iodo-vinyl-pyrimidine, or else BrVaraU bearing $^{125}$I in the wrong position, or else BrVaraU remaining following HPLC. Another term for these substances is "pseudocarrier". The concern is that these substances might interfere with or modify the uptake of radioactive XVaraU. The residues of catalyst, bromine, reducing agents, etc. are not so likely to act as analogues of XVaraU, or interfere with the uptake of XVaraU. These latter substances are removed by the Sep Pak procedure and HPLC, so that they are essentially absent entirely from the final formulation.

As described above in connection with the process, the radiohalogen of the composition, i.e. *X, is most preferably radioactive bromine or iodine, with again iodine being the far preferable radioactive halogen, and particularly $^{123}$I, $^{125}$I and $^{131}$I. Again, most preferably the halogen is $^{123}$I or $^{125}$I. When $^{123}$I or $^{125}$I is the halogen, the reaction proceeds to near ideal criteria, and the composition will consist essentially of only the [$^{123}$I] or [$^{125}$I]IVaraU. That is, the composition will not contain any materials which will materially affect the diagnosis or treatment regimens, other than the [$^{123}$I] or [$^{125}$I]IVaraU. Such a composition, therefore, is quite suitable for treating or detecting particularly difficult virus infections, such as the herpes virus infections, in man. This is particularly true for the HSV type 1 and HSV type 2 herpes virus.

In regard to the composition used for diagnosis, the method of diagnosis for an animal for herpes virus infection comprises administering to the animal a scintillating effective amount of the composition, described above, and preparing a scintigram of the animal. The scintillating/scintigram technique is well known in the art, and need not be described herein, for sake of conciseness, and it will be appreciated that the invention goes to compounds which will provide acceptably sufficient scintigrams for accurate diagnosis. An effective amount of the compound, of course, will depend upon the particular animal, its body weight, and other recognized such factors. However, generally speaking, the dosage should be between 1 and 20 millicuries total for humans and 0.01 to 0.5 millicuries per kilogram in veterinary diagnostic application, based on the [*]XVaraU, for diagnostic purposes.

A second method of diagnosis is that of an analysis for free herpes virus particles in a patient's blood. A sample of the patient's blood is added to tissue culture cells susceptible to herpes infection, e.g. HFF (human foreskin fibroblast) cells, and the composition, described above, is added thereto. The uptake of the radioisotope into the tissue culture cells indicates the quantity of herpes virus in the sample. As can be appreciated, therefore, this blood assay method offers considerable simplification in that the radioisotope is not injected into the patient's body and the assay is suitable for mass screening of the public.

In regard to the method of treating an animal having herpes virus infection, broadly, the method comprises administering to the animal a virus-destructive effective amount of the composition described above. Here again, the dosage can vary widely but, generally speaking, from 5 to 150 millicuries total per day for humans and 0.05 to 3 millicuries per kilogram weight per day in veterinary applications, based on the [*]XVaraU, is sufficient. This method of treatment depends upon the radioactive decay of the composition and is a known method of treatment, referred to as "Auger therapy". The concept of this therapy, generally speaking, is that the radioactive tracer is incorporated into the herpes viral DNA. With the subsequent decay of the radioactive label, e.g. $^{123}$I or $^{125}$I, the radioactivity will damage the viral DNA. It is known from in vitro experiments that a single decay of $^{123}$I or $^{125}$I incorporated, or bound by a ligand, into DNA is sufficient to cause a double-stranded break in the DNA molecule. This breakage is thought to result from Auger electrons emitted during decay.

The invention has been particularly described in connection with the herpes viruses, since these are a particularly intractable virus. Herpes viruses comprise a large group of viruses associated with diseases and are defined as large viruses that have a DNA core, a capsid on its surface, 162 capsomers arranged in the form of an icosahedron, and a lipid-glycoprotein envelope. Some well-known types are Herpes simplex subtype 1, Herpes simplex subtype 2, varicella zoster virus, Herpesvirus T, Herpesvirus saimiri, Human cytomegalovirus, Epstein- Barr virus, Marek's disease virus, and Infectious laryngotracheitis. Various virus species are known which seem to lack virus-specific thymidine kinase, and yet are sensitive to inhibition by bromo vinyl deoxyuridine. While the biochemistry of such viruses is not understood, the invention is nevertheless applicable thereto, as well as being applicable to more common herpes viruses, such as HSV-1 and HSV-2.

It will also be appreciated that the process and composition can use radioisotopes other than those particularly described above. Thus, for example, any of $^{120}I$, $^{121}I$, $^{122}I$, $^{123}I$, $^{124}I$, $^{125}I$, $^{128}I$ and $^{131}I$ can be used. Similarly, any of $^{75}Br$, $^{76}Br$, $^{77}Br$, $^{80}Br$ and $^{82}Br$ can be used.

The invention will now been illustrated by the following examples, where all percentages and ratios are by weight, unless otherwise specified.

EXAMPLE 1

A. A solution of $^{125}I$ ($[^{125}I]NaI$ in 0.1N NaOH, NEN.DUPONT, 5.35 millicuries, in 14 μL total volume) was transferred with several portions of water (5×10 μL) into a 5 mL serum vial. This was sealed with a rubber stopper (Wheaton P/N 224124) and flushed with nitrogen gas (N.F.) for 15 min. Nitrogen flushing was achieved by means of two hypodermic needles (25 GA×5/8 in), one bearing a gas hose.

B. Dilute $H_2SO_4$ (0.01M) was prepared by dispensing 3.1 g distilled water into a serum vial (Wheaton 22378), adding 31 μL of $H_2SO_4$ (1.0M), sealing, and flushing with nitrogen gas for 45 min.

C. The substrate was prepared by weighing out 1.5 mg (E)-5(2 bromo vinyl)-arabinofuranosyl uracil (BrVaraU) into a Wheaton (P/N 223738) 5 mL serum vial, sealing with a rubber septum and crimp, and flushing with nitrogen gas for 15 min. Then, 1.5 mL anaerobic aqueous $H_2SO_4$ (0.01M) was injected into the sealed vial of BrVaraU through the rubber seal by means of a tuberculin syringe (Monoject P/N 8881-501160) equipped with a hypodermic needle (25 GA×2 in) (Monoject P/N 8881-200441). In order to dissolve the BrVaraU, the serum vial with BrVaraU and aqueous $H_2SO_4$ was placed for 1 minute in a heating block (Reacti-Therm, Pierce) set at 95° C. The vial was then withdrawn, rocked by hand for about 2 min. until the last BrVaraU crystals dissolved, and cooled to room temperature.

D. Reductants were prepared in advance by trituration of cupric sulfate pentahydrate (30 mg), ascorbic acid (2.0 g), and stannous sulfate (100 mg) with a mortar and pestle, and weighing out 12 mg of the mixture into a regular serum vial (Wheaton P/N 223738), sealing, and flushing with nitrogen 15 min. In the labelling procedure, a volume of 1.2 mL of solution BrVaraU in aqueous $H_2SO_4$(B) was transferred to the dry reductants by means of a tuberculin syringe with (25 GA ×2 in) hypodermic needle.

E. 1.0 mL of the solution of unlabelled ingredients (D) i.e. BrVaraU, aqueous $H_2SO_4$, copper salt, and reducing agents) was injected into the $^{125}I$ solution (A) in the conical vial by means of a tuberculin syringe with hypodermic needle (25 GA×2 in) and subsequently flushed with nitrogen gas for 1 min. Finally, the conical vial was set in a heating block (95° C.) (Reacti-Therm, Pierce).

Heating was continued for 60 minutes, and then the reaction mixture was cooled to room temperature.

Thin layer chromatography: A small sample was diluted in methanol to give approximately 100 μCi/mL. 10 μL of the diluted sample was applied at the origin (1.0 cm) of a Bakerflex (T.M.) IB2F silica gel thin layer sheet (5 cm×20 cm) and was run 30 min in the solvent chloroform/methanol (80/20 by volume). At the end of this time the sheet was dried, covered with adhesive plastic tape, and cut into 1 cm segments. The segments were counted in a Beckman Gamma 8000 counter (*IVaraU: $R_f$=0.75; iodide: $R_f$=0.12). The result was 93.3% radiochemical purity.

A Waters SEP-PAK (T.M.) C18 cartridge (P/N 51910) was prepared with methanol and water washed. The labelling mixture was applied to the SEP-PAK by means of an injection with a plastic syringe (5 mL). Two washes of the reaction vial were performed using water (2×1.0 mL) likewise passed through the SEP-PAK using the syringe. The SEP-PAK was then washed using distilled water (2×5 mL) and then air (2×5 mL) was passed through the cartridge by using the plastic syringe.

The radioactive nucleoside was eluted from the cartridge by applying acetonitrile (1.5 mL). The acetonitrile was collected in a conical plastic micro centrifuge tube, which was placed in a water bath at 80° C.; the acetonitrile was evaporated to approximately 0.4 mL under a stream of $N_2$.

High performance liquid chromatography: A Phenomenex Bond clone column (10-C18-7.8 mm×300 mm) was used with a solvent of acetonitrile (20%) in water (80%). The flow rate was 2.5 mL/min. The supporting equipment included Rheodyne injector, Gilson pump and UV detector (292 nm), and Beckman gamma ray detector. The reduced volume acetonitrile solution was injected as a single bolus, and the $[^{125}I]IVaraU$ fraction was recovered for further use. (Retention times: BrVaraU, tr=10.1 min.; IVaraU, tr=12.5 min., [*I] iodide, tr=3.0 min.) Approximately 5 mL product was recovered off the HPLC. This solution was evaporated to dryness under an $N_2$ stream at room temperature, and then used in the in vitro tissue culture assays. The quantity recovered was 87.7%.

A labelling of 300 μg BrVaraU with $^{125}I$ using only 15 min. heating was conducted in the same manner described above, with two exceptions: only 1 mCi $^{125}I$ (in 3 μl ) was used, 10 mg reductants, 300 μL total solution, and a conical vial (manufactured from the standard Wheaton) were used, and the final heating at 103° (block) was carried out for 15 min. Thin layer chromatography gave 85.2% radiochemical purity.

Two other labellings were performed as described above, with the following exceptions: $^{123}I$ was used in place of $^{125}I$. The portions used for an individual labelling were as follows: $^{123}I$ (1.0 μL, 0.1 N NaOH, Nordion, 0.26 mCi) was placed in a regular serum vial with added water (100 μL), sealed, and flushed with $N_2$.

BrVaraU (3 mg) was suspended in dilute $H_2SO_4$ (500 μL) by briefly heating with a heating block set at 95° C. The resulting solution was added to ascorbic acid (9.5 mg) $SnSO_4$ 500 μg, and $CuSO_4.5H_2O$ (150 μg) using the above precautions, and finally transferred to the $^{123}I$ vial. Heating was for 30 min. at 90° C. block temperature.

A second sample was processed exactly as described above, but $CuSO_4$ was entirely omitted. Thin layer chromatography results of radiochemical purity were 99.0% $[^{123}I]IVaraU$ with copper and 8.1% $[^{123}I]IVaraU$ without copper.

Also, 100 μg BrVaraU was labelled with 20 mCi $^{123}I$: $^{123}I$ ($[^{123}I]NaI$ in 0.1N NaOH, 20 μL, 20 mCi, Nordion)

was dispensed into a conical serum vial along with water (10 μL) and dilute $H_2SO_4$ (0.05N, 15 μL), was sealed, and flushed with nitrogen for 30 min.

A solution of BrVaraU (1.6 mL, 1.0 mg/mL) was prepared as above, and 1.0 mL was injected into reductants which consisted of ascorbic acid (9.5 mg), $SnSO_4$ (0.5 mg) and $CuSO_4.5H_2O$ (150 μg). Out of the latter solution, 100 μL was injected into the $^{123}$I vial. After 2 min. $N_2$ flushing, the mixture was heated 30 min. in a block set at 100° C. Thin layer chromatography showed 94.0% radiochemical purity.

EXAMPLE 2

Upright roller tubes were seeded with $1.5 \times 10^5$ HFF (Human Foreskin Fibroblast) cells/tube in a volume of 1.0 ml of Minimal Essential Medium (MEM) with added 5% FCS (Fetal Calf Serum) and incubated at 37° C. overnight. The growth media was poured off and replaced with 1.0 ml of viral growth media (Med 199 Hank's salts with 2% FCS) containing $^{125}$I-IVaraU ($2.3 \times 10^6$ cpm/ml). 100 μl of virus (diluted to appropriate concentration in viral growth media) was added to assay tubes. In this case, a multiplicity of infection of 1.0 was used. 100 μl of viral growth media was added to the control (viral uninoculated) tubes.

The tubes were centrifuged 5000 g×30 minutes at 37° C., incubated at 37° C., 5% $CO_2$ for 6 hours, and the media was then poured off. The tubes were washed with 4×2 mls warm "cell" phosphate buffered saline (PBS), and 1.0 ml of trypsin-versene solution was added and the tubes were incubated at 37° C. for 5-10 minutes. The cell sheets were removed and transferred to 4 ml polystyrene tubes. The gamma activity was counted with a Gamma counter.

RESULTS

| Virus Type (Strain) | Activity/Tube (Average) |
|---|---|
| HSV-1 (ATCC Strain F) | 59,914 cpm |
| HSV-2 (ATCC Strain G) | 14,462 cpm |
| Control (uninoculated) | 1,332 cpm |

Similar procedures were used to measure the uptake of [$^{123}$I]IVaraU and [$^{125}$I]IVaraU in tissue cultures, namely, the overall percent of [$^{123}$I]IVaraU or {[$^{125}$I]IVaraU assimilated from liquid medium with HSV 1 and HSV 2 infected cells, where present copper-processed no-carrier-added compositions were compared with carrier-added (trimethylsilylvinyl) compositions. Overall, the present no-carrier-added compositions had an average assimilation of 27.1%, as compared with an average 8.3% for the compared carrier-added compositions. This shows a superior uptake of the present no-carrier-added compositions. Further, the data showed that the present copper-processed [$^{125}$I]IVaraU was taken up specifically by HSV 1 infected cells, as compared with uninfected cells, and the HSV 1 infected cells took up more radio compound than HSV 2 infected cells. Thus, on average, the present no-carrier-added compositions have 3.3 times the uptake (or resolution) as comparable carrier-added compositions.

EXAMPLE 3

Experimental

This example measured the biodistribution of [$^{125}$I]-IVaraU in the bodies of mice infected with HSV throughout the entire body. The brain was emphasized. Various uninfected controls were included to make the interpretation clear.

800 strain A/J mice were used in all: (i) with [$^{125}$I]IVaraU, 20 mice received HSV1 and 20 mice were uninfected; and (ii) with [$^{125}$I]NaI (a control compared to IVaraU), again 20 mice received HSV1 and 20 mice were uninfected.

METHOD

INFECTION: Seven days prior to injection of the drug, each A/J mouse was inoculated by scratching the lip and applying a suspension of herpes simplex virus 1 (HSV1); this was the Kastrukoff murine-adapted strain of HSV1. This inoculation technique is a literature technique which has been established to cause herpes foci of herpes infection in the brains of over 99% of mice so inoculated. See Kastrukoff LF, Lau AS, and Puterman ML. J Gen Virol 67 (1986) 613-621. The HSV1 inoculation may be considered to take place at time "zero minus seven days". ADMINISTRATION OF THE RADIOPHARMACEUTICAL: The mice were divided into four experimental groups based on the two variables +/- HSV1, and IVaraU/NaI. The infected mice were being compared to non-infected mice. The radiopharmaceutical ([$^{125}$I]IVaraU or [$^{125}$I]NaI) was diluted to give 1μ Curie per 100 μL. 100 μL was then injected into the tailvein of each mouse. (Injection may be considered to take place at "time zero".) ANALYSIS OF INDIVIDUAL BODY ORGANS: At times 1h, 4h, 24h, and 48h, 5 mice were taken from each experimental group and sacrificed by exsanguination (the carotid artery was severed with a surgical scalpel). Blood was collected. Each animal was dissected, and the following organs were removed: brain, liver, kidney, pancreas, spleen, stomach, heart, lung, and muscle. Each organ or tissue specimen was weighed and then $^{125}$I activity was counted in a gamma ray counter. From the data weight, $^{125}$I, and $^{125}$I injected dose result values of "% dose per gram" were calculated for the different tissue specimens.

The number of result data was large: 80 mice ×10 data per mouse gave 800 result data in all, but a summary of results is given below.

RESULTS

| BRAIN UPTAKE ANALYSIS: % dose per gram in entire brain: | | | |
|---|---|---|---|
| Time | Infected | Uninfected | Ratio |
| 1H | 1.4936 | 1.2651 | 1.18 |
| 4H | 0.3599 | 0.2294 | 1.57 |
| 24H | 0.0379 | 0.0024 | 15.8 |
| 48H | 0.0181 | 0.0005 | 36.2 |

It can be seen that the infected/non-infected ratio was 36.2 to 1 at 48 hours. DEMONSTRATION THAT THE BRAIN WAS ACTUALLY INFECTED WITH HSV1: A random sampling was made to select 10 of the infected brains. A small piece was excised from each brain, freeze dried, ground up, and the paste was inoculated into a Vero cell culture (African green monkey cells). The tissue culture was later examined by microscope for cells which were rounded up in a characteristic well-known cytopathic appearance. The result was that all 10/10 brains were judged to be infected. The assay is described in the literature as follows: Kastrukoff FF, Lau AS, and Kim SY. Ann Neurol 22 (1987)

52–59; Kastrukoff FF, Hamada T, and Schumaker U. J. Neuroimmunol 2 (1982) 295–305.

EXAMPLE 4

This example examined [$^{125}$I]IVaraU uptake in a rabbit brain infected with HSV1 and determined whether the uptake of [$^{125}$I]IVaraU is higher in infected than non-infected areas of the brain.

The rabbit brains were infected with HSV1 and then [$^{125}$I]IVaraU was injected. The infection was located by assaying for herpes antigen and also by considering the brain anatomy involved. The assay was performed for [$^{125}$I]IVaraU by gamma ray counts on segments cut from the brain.

METHOD

INFECTION: Three New Zealand White female rabbits (4–6 weeks old, 2.5–5.0 kg) were anaesthetized by standard intramuscular injections of ketamine and xylazine. A 3.5 inch french tomcat catheter was introduced into the right nostril and 100 μL of the virus inoculation solution was released onto the right cribiform plate (this is a non-invasive means to create a brain infection). The virus inoculation solution consisted of $3.7 \times 10^6$ plaque forming units per mL HSV1 strain KOS suspended in commercial media of the type "199 with Hanks' salts". Two rabbits denoted "A" and "B" received the virus suspension exactly as described. A third rabbit denoted "C" was a "control"; it received 100 μL "199 with Hanks' salts" but no virus. The three rabbits were returned to their cages; infection was allowed to develop for 5 days before the injection of [$^{125}$I]VaraU was carried out. INJECTION OF DRUG: 5 days following HSV1 inoculation, each rabbit was given 0.1 to 0.2 millicuries [$^{125}$I]IVaraU suspended in 1 mL standard phosphate buffered saline PBS). The drug was administered by injection into the right marginal ear vein. SACRIFICE OF THE RABBITS: 24H after the [$^{125}$I]IVaraU injection, the rabbits were sacrificed by an overdose of the drug Somnotol (T.M.) (MTC Pharmaceuticals). Following death, each rabbit was perfused with 300–400 mL PBS introduced into the ascending aorta. (The perfusion procedure served to remove blood from vessels in the brain and the body in general.)

The skull was dissected; the brain was cut out and removed. The brain was then sectioned into thirty 0.5 cm thick coronal blocks. The cutting and numbering of the blocks was carried out in a systematic way with respect to brain anatomy. Brain blocks were immersed and stored in 10% formalin. COUNTING OF $^{125}$I ACTIVITY IN BRAIN BLOCKS: Each block was weighed and then counted in a well-type gamma ray counter. The "counts per minute per gram" was calculated for each block of tissue for rabbits "A", "B" and "C". From each "cpm per gram" in infected rabbits "A" and "B" was subtracted the "cpm per gram" in the corresponding brain block from the uninfected rabbit "C". (The typical value of "cpm per gram" was about 20,000 cpm per gram in rabbit "C".)

The data showed that the (corrected) activities are higher in the forebrain, especially in the olfactory lobes. The activity is higher in the right olfactory lobe than the left. Similarly, the activity in the right olfactory lobe was higher than in the trigeminal ganglia and Level 1. As one progressed to the hindbrain, the activities approached background. PREPARATION OF THIN SLICES FOR HISTOLOGICAL ANALYSIS: Brain blocks were removed from 10% formalin and dehydrated by soaking in ascending concentrations of ethanol (70-95-100%) and then in xylene. The xylene-saturated brain blocks were placed in microtome cassette receptacles and embedded in paraffin wax.

The paraffin blocks were sliced into 5 μm sections which were floated on a warm water bath. Sequential sections were then adhered to silane-coated microscope slides. Sections were fixed onto the glass slides by holding each slide over a hotplate until the paraffin melted. At all times, the original relative order of the sections was preserved. The slice thickness of 5 μm allowed 3 or more sections to be made cutting through the same neuron. By keeping the slices in strict order, one could make several analyses on the same neuron or microregion of the brain. The cooled slides were deparaffinized in xylene and then brought back to the aqueous state by washing in descending concentrations of ethanol (100-95-70%). IMMUNOHISTOCHEMISTRY (LOCALIZATION OF HERPES AND CELL-TYPE ANTIGENS): The tissue sections were washed in two changes of phosphate buffer to remove ethanol, two changes of distilled water to remove salts, and then allowed to dry. A ring of Duco cement was set up encircling each tissue section; this provided a "well" to retain subsequent reagents.

The antibody assay was a "horseradish peroxidase" staining type assay. A commercial kit, the Vectastain (Victor) (T.M.) ABC immunohistochemistry kit with enclosed reagents and instructions was used.

1. "Blocking agent" was made up of 0.1% bovine serum albumin, 0.1% normal rabbit serum, and 0.1% normal mouse serum in PBS. 200 μL blocking agent was added to each well and incubated 2 hours at room temperature (RT). The purpose of blocking agent is to reduce non-specific staining.

2. Sections were decanted of blocking solution. A 1/100 to 1/2000 dilution of the appropriate antibody was selected from the following list, added to the well, and incubated for 2 hours at RT:

| | |
|---|---|
| 2.1: anti-HSV: | This was a polyclonal IgG raised in a rabbit against the HSV1 McIntyre strain. This preparation cross reacts with the HSV1 KOS stain. |
| 2.2: anti-neuron: | This was a monoclonal antibody raised from mouse cells against neurofilament. |
| 2.3: anti-astrocyte: | This was also a mouse monoclonal antibody, directed against fibulary acidic protein. |
| 2.4: anti-oligodendrocyte: | This was also a mouse monoclonal antibody, directed to myelin basic protein. |

Summary: Antibody type 2.1 will bind to herpes antigen, while types 2.2, 2.3 and 2.4 will bind to specific cell types found in the brain. Only neurons (2.2) are regularly infected with HSV.

3. Sections were washed in 3 changes of PBS by dipping slides in PBS.

4. Sections were treated with biotinylated antibody for 2 hours at RT in a humidified chamber. The biotinylated antibody was goat polyclonal anti-rabbit-IgG (for 2.1) or else goat polyclonal anti-mouse-IgG (for 2.2, 2.3 or 2.4).

5. Sections were washed in 3 changes of PBS.

6. A reagent composed of avidin conjugated to horseradish peroxidase (HRP) was diluted 1/600 in PBS and incubated with the tissue section 1 hour at RT. The avidin binds to biotin and thus bring the HRP into close proximity to the goat and rabbit antibodies and the target antigen.

7. Sections were reacted with a solution of diaminobenzydine (prepared from the Vectastain kit) in reduced light at RT for 2-15 minutes. The reaction was stopped by 3 incubations of 20 minutes each in phosphate buffer (0.1M, pH 7.4). Sections were dipped briefly in 2 changes of distilled water to remove the salts and allowed to dry.

8. Dry sections were treated in ascending concentrations of ethanol (95-100%) and then xylene. Sections were then mounted with Permount (T.M.) and then coverslipped.

RESULTS

Target antigen was seen as brown stain by eye and under microscope; the stain is a result of the reaction of the dye DAB with the HRP. HSV1 antigen was observed by eye as brown patches a few mm$^2$ in extent. The patches were only observed in the brains of infected rabbits, not in the uninfected rabbit. In infected rabbits, the brown patches were only observed in the olfactory bulbs on the right-hand side, not on the left side or other regions of the brain.

What is claimed is:

1. A process for producing (*X)XVaraU comprising reacting (*X)X$^-$ with YVaraU in the presence of cuprous ion catalyst under anaerobic and reducing conditions, where (*X)X$^-$ is radioactive iodide or bromide, Y is iodine or bromine, X and Y are different, and XVaraU is 1-(B-D-arabinofuranosyl)-5(E)-(2-halogenovinyl) uracil, the halogen of which is X.

2. The process of claim 1 wherein X is iodine and Y is bromine.

3. The process of claim 2 where *X is $^{123}$I, $^{125}$I or $^{131}$I.

4. The process of claim 1 wherein the reaction is carried out in the presence of a reducing agent selected from the group consisting of ascorbic acid, dihydroxybenzoic acid, and a stannous tin salt.

5. The process of claim 4 wherein the reducing agents are ascorbic acid and SnSO$_4$.

6. The process of claim 1 wherein the reaction is carried out in the presence of an anion selected from the group consisting of a sulfate, acetate and phosphate anion.

7. The process of claim 6 wherein the anion is a sulfate anion.

8. The process of claim 1 wherein the cuprous ion catalyst is provided in situ by a cupric salt.

9. The process of claim 8 wherein the salt is CuSO$_4$.

10. The process of claim 1 wherein the anaerobic conditions are provided by a blanket of inert gas.

11. The process of claim 1 wherein the reaction is carried out in a solvent selected from the group consisting of water and tert. butyl alcohol.

12. The process of claim 11 wherein the solvent is water.

13. The process of claim 1 wherein the reaction is carried out at an elevated temperature of at least 50° C.

14. The process of claim 13 wherein the elevated temperature is at least 75° C.

15. The process of claim 14 wherein the elevated temperature is about 100° C. to 125° C.

* * * * *